United States Patent
Enzelberger

(10) Patent No.: US 8,759,087 B2
(45) Date of Patent: Jun. 24, 2014

(54) INTERNALIZATION

(75) Inventor: Markus Enzelberger, Planegg (DE)

(73) Assignee: Morpho Sys AG, Martinsried (DE)

( * ) Notice: Subject to any disclaimer, the term of this patent is extended or adjusted under 35 U.S.C. 154(b) by 352 days.

(21) Appl. No.: 12/518,439

(22) PCT Filed: Dec. 12, 2007

(86) PCT No.: PCT/EP2007/063843
§ 371 (c)(1),
(2), (4) Date: Jun. 10, 2009

(87) PCT Pub. No.: WO2008/071749
PCT Pub. Date: Jun. 19, 2008

(65) Prior Publication Data
US 2010/0016553 A1    Jan. 21, 2010

Related U.S. Application Data

(60) Provisional application No. 60/869,652, filed on Dec. 12, 2006.

(51) Int. Cl.
*C12N 15/10* (2006.01)
*C12N 15/70* (2006.01)
*C12N 15/64* (2006.01)

(52) U.S. Cl.
CPC .................................. *C12N 15/1037* (2013.01)
USPC ........................................ 435/320.1; 435/472

(58) Field of Classification Search
None
See application file for complete search history.

(56) References Cited

FOREIGN PATENT DOCUMENTS

| WO | WO99/10485 | 3/1999 |
|---|---|---|
| WO | WO/99/55367 | 11/1999 |
| WO | WO00/29555 | 5/2000 |
| WO | WO/00/61190 | 10/2000 |
| WO | WO/01/05950 | 1/2001 |
| WO | WO02/094995 | 11/2002 |

OTHER PUBLICATIONS

Barry et al., Nature Medicine, 2 (3) 299-305, 1996.*
Nielsen et al., Biochimica Et Biophysica Acta. Molecular Cell Research, Aug. 19, 2002, p. 109-118, vol. 1591,No. 1-3, Elsevier Science Publishers, Amsterdam, NL.
Poul et. al., J. of Mol. Biol.. Sep. 1, 2000, p. 1149-1161, col. 301, No. 5, London GB.
Hart, et al.: "Cell Binding and Internalization by Filamentous Phage Displaying a Cyclic Arg-Gly-Asp-containing Peptide"; J. Biol. Chem. vol. 269, No. 17, Issue of Apr. 29, pp. 12468-12474, 1994.
Krumpe & Mori: "The Use of Phage-Displayed Peptide Libraries to Develop Tumor-Targeting Drugs", International Journal of Peptide Research and Therapeutics, vol. 12, No. 1, Mar. 2006 (2006), pp. 79-91.

* cited by examiner

*Primary Examiner* — Nancy T Vogel
(74) *Attorney, Agent, or Firm* — Paul F. Wiegel

(57) ABSTRACT

A target internalized within a cell (and a binding member that specifically binds thereto) can be identified in an efficient manner by segregating (or substantially segregating) genetic material encoding the binding member from genetic material encoding a binding member that binds to a target that is not internalized. This can be achieved by employing a display library of binding members having a genotype/phenotype linkage via a non-fusion protein format, whereby genetic material encoding non-in-ternalized targets can be segregated (or substantially segregated) without lysing the cells. Internalized genetic material subsequently can be isolated and amplified.

7 Claims, 2 Drawing Sheets

Efficiency of target internalization upon Fab binding.

Efficiency of phage target complex internalization and depletion of surface bound phage by DDT.

INTERNALIZATION

CROSS-REFERENCE TO RELATED APPLICATION

This application claims the benefit of U.S. provisional application Ser. No. 60/869,652 filed Dec. 12, 2006.

A variety of documents is cited in this specification. The disclosure content of these prior art documents, including manufactorer's manuals, is herewith incorporated by reference in its entirety.

BACKGROUND OF THE INVENTION

New targets have been identified by comparative and statistical analysis of healthy and diseased patients, in particular by analyzing tissues and/or blood derived plasma from said patients. Usually, the comparative analysis can be done on different levels, such as on DNA-, RNA-, protein- and post translational levels. One commonly used technique is based on differential gene expression analysis. Briefly, mRNA derived from both, diseased and healthy cells is labeled and subsequently hybridised to a gene chip and quantified. Up- or downregulation of different mRNAs, as derived from the quantification signals, reveals potential new targets. Another approach well known in the prior art is based on the identification and comparison of DNA methylation patterns of DNA molecules derived from healthy and diseased patients.

It is to be noted in the above context, however, that neither the DNA modification (i.e. the DNA methylation pattern) nor the differential gene expression analysis (i.e. the level of mRNA expressed in a cell) necessarily reflects whether a specific protein encoded by the corresponding DNA or the corresponding mRNA is indeed expressed. Therefore, identification of differential expression levels, i.e. quantitative and also qualitative analysis of protein expression patterns of healthy as compared to diseased cells, remains challenging.

A method for identification of differential protein expression levels is based on differential two-dimensional gel analysis of said proteins with subsequent analysis via mass spectrometry, a technique well known to the person skilled in the art. Additionally, methods based on protein fractionation, such as, to mention but a few, techniques based on the use of protein chips, HPLC- and FPLC related techniques which are all known to a person skilled in the art.

Techniques of phage display offer, for example, the possibility to deplete a large library, e.g., an expression library of binding members, on samples, such as tissues or cells that are, for example, derived from a healthy donor, and use the residual population of the library on samples, such as tissues or cells, that are derived, for example, from a diseased donor. Binding members which have been traced by depletion analysis, i.e. which bind to (poly)peptide targets or counterparts of diseased tissues/cells but not to healthy tissues/cells are usually considered to bind to a target which is uniquely (or at least much higher) expressed on the target cells (e.g. the diseased cell). Subsequently, binding member/(poly)peptide target complexes can be identified by, e.g., mass spectrometry or methods for protein analysis well known to the person skilled in the art.

Of particular interest are binding members that internalize upon binding of their target. A person skilled in the art is aware that said binding members can, e.g., then be fused to any substance or any small molecule that might be toxic for the cell thus triggering the killing of the, preferably diseased, cell expressing said target(s), which cell preferably is diseased. As also known in the art, once a target of interest that internalizes has been identified as, e.g., a diseased or cancerous cell, it is then possible to determine further binding members with, e.g., higher affinity to the target and/or higher potential for triggering internalization of said target. Said improved binding members can then be considered, for example, as drugs for treating, e.g., diseased cells expressing said target(s).

To efficiently determine potential targets that have internalized into the cell upon binding of their respective binding member, it would be desirable to separate internalized complexes from non internalized complexes. However, in the prior art, said separation has not been achieved in a qualitative and quantitative satisfying manner thus confronting the skilled artisan with time consuming and complex techniques for determining binding members and targets that internalize.

There is therefore a continuous need to further develop and also ameliorate methods and processes that allow for efficient separation between internalized and non-internalized complexes.

Percent (%)-internalization was calculated from the ratio of extracellular signal on cell surface at 4° C. vs. 37° C.; recovery of fluorescence was measured by the ratio of extracellular plus intracellular staining at 4° C. vs. 37° C., showing that no or only few phage particles were lost during the internalization process, the saporin treatment and/or the staining. Fab A showed an 80% internalization, Fab B only internalized with 20%, and Fab C showed no binding at all.

Figure 2:
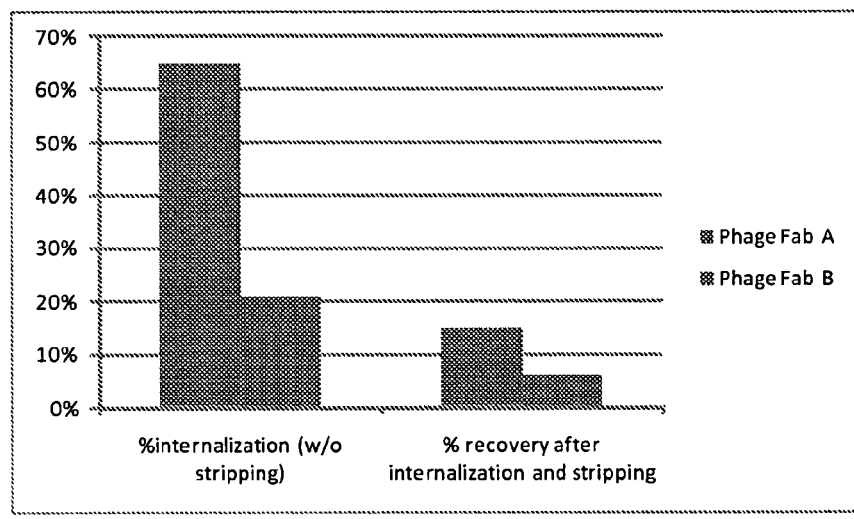

FIG. 2 shows efficiency of phage target complex internalization and depletion of surface bound phage by DDT.

Internalization of phages displaying via a disulfide bond Fab A against an antigen that predominantly internalizes versus phages displaying via a disulfide bond a Fab B against an antigen that does not predominantly internalize is shown.

Percent (%)-internalization was calculated from the ratio of extracellular signal on cell surface at 4° C. vs. 37° C.; recovery of fluorescence was measured by the ratio of extracellular plus intracellular staining at 4° C. vs. 37° C.

DETAILED DESCRIPTION OF THE INVENTION

The present invention relates, in one aspect, to a method for recovering a nucleic acid molecule encoding a binding member of a complex internalized in a cell, comprising the following steps of (a) contacting a cell with a diverse collection of bacteriophage particles, wherein each or substantially all of said bacteriophage particles displays a binding member on its surface, wherein said binding member is displayed as a non-fusion (poly)peptide with a phage coat protein of said bacteriophage particle and wherein each or substantially all of said bacteriophage particles comprises a nucleic acid molecule encoding the displayed binding member, (b) allowing for binding of the binding member displayed on the bacteriophage particle to its target, thereby allowing for the formation of at least one complex, each of said complexes comprising a bacteriophage particle with its displayed binding member and its target, (c) culturing the cell under conditions that allow internalization of at least one of said complexes into the cell, (d) eluting the nucleic acid molecules encoding a binding member that are not internalized under conditions that substantially no cell lysis occurs, (e) lysing the cell comprising the internalized complexes, and (f) recovering from the lysed cell the nucleic acid molecule encoding a binding member derived from at least one of the internalized complexes.

The term "cell" refers to any eukaryotic or prokaryotic cell. Preferred in connection with the present invention are mammalian cells. Mammalian cells may comprise healthy and also diseased cells.

In the context of the present invention, the term "diverse collection" refers to a collection of at least two particles or molecules which differ in at least part of their compositions, properties, and/or sequences.

The term "a diverse collection of bacteriophage particles" as used in connection with the present invention refers to a plurality of bacteriophage particles. Each or substantially all members of such a plurality display a distinct binding member. Methods for the generation of diverse collections of bacteriophage particles are well-known to one of ordinary skill in the art.

The term "bacteriophage" as used in connection with the present invention is to be construed in its broadest sense. In the context of the present invention, the term "bacteriophage" therefore relates to any bacterial virus that forms a package having a protein coat containing nucleic acid required for the replication of the phage. The nucleic acid may be DNA or RNA, either double or single stranded, linear or circular. Bacteriophage such as phage lambda or filamentous phage (such as M13, fd, or fl) are well known to the artisan of ordinary skill in the art.

Preferred in the context of the present invention is a filamentous bacteriophage, such as, for example, M13 bacteriophage. More preferred is the filamentous bacteriophage VCSM 13.

In the context of the present invention, the term "bacteriophage particles" refers to the particles according to the present invention, i.e. to particles displaying a (poly)peptide/protein.

In the above context, it is to be considered that each or substantially all members of the diverse collection of bacteriophage particles display a binding member, wherein each binding member preferably differs in at least one amino acid position of their sequence.

The term "binding member" in accordance with the present invention refers to any (poly)peptide that can bind to a specific counterpart or target, thereby forming a complex. Said term, in connection with the present invention, is construed to comprise, inter alia, any scaffold known to a skilled artisan. A "scaffold" in connection with the present invention refers to any collection of (poly)peptides having a common framework and at least one variable region. Scaffolds known to the skilled artisan are, for example, fibronectin based scaffolds or ankyrin repeat protein based scaffolds. The term "(poly)peptide" as used herein describes a group of molecules which comprise the group of peptides, as well as the group of polypeptides. The group of peptides is consisting of molecules with up to 30 amino acids, the group of polypeptides or proteins is consisting of molecules with more than 30 amino acids. The term "(poly)peptide" in connection with the present invention is construed to also comprise an antibody or antibody fragment or derivative thereof. Said antibody is to be construed to comprise any immunoglobulin known to the skilled artisan. An "immunoglobulin" (Ig) is protein belonging to the class IgG, IgM, IgE, IgA, or IgD (or any subclass thereof), and includes all conventionally known antibodies and functional fragments thereof. A "functional fragment" of an antibody/immunoglobulin hereby is defined as a fragment of an antibody/immunoglobulin (e.g., a variable region of an IgG) that retains the antigen-binding region. The term "antibody fragment or derivative thereof" relates to single chain antibodies, or fragments thereof, synthetic antibodies, antibody fragments, such as Fab, a F(ab2)', Fv or scFv fragments, single domain antibodies etc., or a chemically modified derivative of any of these. Antibodies to be employed in accordance with the invention or their corresponding immunoglobulin chain(s) can be further modified outside the motifs using conventional techniques known in the art, for example, by using amino acid deletion(s), insertion(s), substitution(s), addition(s), and/or recombination(s) and/or any other modification(s) (e.g. posttranslational and chemical modifications, such as glycosylation and phosphorylation) known in the art either alone or in combination. Methods for introducing such modifications in the DNA sequence underlying the amino acid sequence of an immunoglobulin chain are well known to the person skilled in the art; see, e.g., Sambrook et al.; Molecular Cloning: A Laboratory Manual; Cold Spring Harbor Laboratory Press, 2nd edition 1989 and 3rd edition 2001.

Fragments or derivatives of the recited antibody molecules define (poly)peptides which are parts of the above antibody molecules and/or which are modified by chemical/biochemical or molecular biological methods. The same applies, mutatis mutandis, to any scaffold. Corresponding methods are known in the art and described inter alia in laboratory manuals (see Sambrook et al., loc cit.; Gerhardt et al.; Methods for General and Molecular Bacteriology; ASM Press, 1994; Lefkovits; Immunology Methods Manual: The Comprehensive Sourcebook of Techniques; Academic Press, 1997; Golemis; Protein-Protein Interactions: A Molecular Cloning Manual; Cold Spring Harbor Laboratory Press, 2002).

The term "is displayed as a non-fusion (poly)peptide" in the context of the present invention refers to any (poly)peptide that is not displayed via any of the conventional fusion techniques known to a person skilled in the art. Conventional display can be achieved, for example, by genetic fusion wherein a fusion protein results as an expression product from the fusion of preferably two genes. A skilled artisan is aware that said fusion protein in the prior art sometimes is referred to as a hybrid or a chimeric protein, which is created by the expression of a hybrid gene, made by genetic engineering and wherein preferably two separate gene sequences are combined.

The term "phage coat protein" in connection with the present invention is considered to comprise not only phage coat proteins derived from any phage well known to the skilled artisan, but also fragments derived therefrom, wherein said fragments are capable of being incorporated into the protein coat of the bacteriophage particle.

The term "target" as used in connection with the present invention refers to (i) any (poly)peptide expressed on a cell that can bind a binding member or (ii) any molecule capable of being internalized into a cell, and which can bind a binding member. Preferred are any cell surface receptors, more preferred receptor tyrosine kinases. The targets comprise any target not known to a skilled artisan and yet to be identified or might be known per se but not in the context of their capacity of internalization. A cell expressing at least one of the potential targets is also referred to in connection with the present invention as a "target cell".

The term "allowing internalization of at least one of said complexes into the cell" refers to any technique well known to a skilled artisan to trigger internalization of the complex into the cell. Preferred are techniques relying on temperature shifts, such as, for example, increasing the temperature from 4° C. to 37° C.

The term "substantially no cell lysis" in the term "eluting the nucleic acid molecules encoding a binding member that are not internalized under conditions that substantially no cell lysis occurs" as used in connection with the present invention is to be construed that not more than approximately 50%, preferably approximately 40%, more preferably approximately 30%, more preferably approximately 20%, preferably not more than approximately 10%, more preferably not more than approximately 5%, even more preferably not more than approximately 1% of the cells are lysed and most preferably none of the cells are lysed.

The term "lysing the cell comprising the internalized complex" as used in connection with the present invention comprises any techniques for lysing cells known to a skilled artisan. As regards mammalian cells, lysis due to the presence of triethylamin is preferred.

As has been outlined above and in other terms, the invention solves the recited technical problem by providing a method that reliably and efficiently allows the skilled artisan to distinguish between internalized and non internalized complexes. With the display techniques based on fusion proteins, a separation of internalized and non-internalized complexes can usually only be achieved by applying rather harsh elution steps with appropriate buffers, such as by using pH- or salt gradients, in order to also deplete the high affinity binding members. Unpredictable cell lysis events result, leading to a mixture of internalized and non-internalized complexes complicating or even preventing any further analysis. The present invention overcomes the above situation, by transferring the advantages of non-fusion display systems, such as, for example, mild elution conditions and independence of the specific affinity between binding member and target, to the field of internalizing complexes.

In a preferred embodiment, a method of the present invention further comprises the step of determining the sequence of the target of the internalized complex. The skilled artisan is aware of techniques for determining the sequence of targets of internalized complexes. Preferably, techniques for determining the amino acid sequence of a (poly)peptide target are contemplated. Reference is also made to the embodiments further below.

In another preferred embodiment of the method of the present invention, said display as a non-fusion (poly)peptide is characterized by a non-peptide bond between the phage coat protein and the binding member.

In a more preferred embodiment of the method of the present invention, said non-peptide bond is a disulfide bond.

In a most preferred embodiment of the present invention, said disulfide bond is generated between a first cysteine residue comprised in said phage coat protein and a second cysteine residue comprised in said binding member.

In another most preferred embodiment of the method of the present invention, said elution of said nucleic acid molecules encoding a binding member that are not internalized is carried out under reducing conditions such that said disulfide bond is cleaved.

This and the previous embodiment refer to a situation wherein the disulfide bond is responsible for the attachment. Details of the above system are disclosed in the patent application WO 01/05950, the contents of which is expressly incorporated herein by reference.

In a preferred embodiment of the method of the present invention, said recovery from the lysed cell of said nucleic acid molecule encoding the binding member is achieved by PCR. In the context of this preferred embodiment, PCR primers can, for example, be used which are capable of amplifying a binding member of interest. Techniques based on specific primers for amplification of nucleic acid molecules by polymerase chain reaction (PCR) are well known to the skilled artisan.

In another embodiment of the method of the present invention said step of determining the sequence of the target in the internalized complex is achieved by mass spectrometry.

The person skilled in the art is aware of techniques for recovering from lysed cells nucleic acid molecules and of techniques for determining the sequence of a (poly)peptide in a complex.

The present invention also relates to a target and/or a binding member obtainable by the method of the present invention.

Finally, the present invention relates to a method for delivering a toxic substance into a cell comprising the steps of (a) obtaining a (poly)peptide encoded by the recovered nucleic acid molecule of claim 1, (b) combining said toxic substance with said (poly)peptide encoded by the recovered nucleic acid of claim 1, and (c) administering to a cell the toxic substance resulting from step (b), thereby triggering internalization of said toxic substance into the cell.

As mentioned above and in other words, the present invention can be used for identifying binding members and/or targets which have the potential to internalize into cells. Preferably, as explained above, said binding members and/or targets can be applied in connection, for example, with the killing of diseased cells, such as cancerous cells. It is to be noted, however, that any application whatsoever known to the skilled artisan and based on the identification of binding members and/or targets capable of internalizing into a cell, is construed to be comprised in the scope of the present invention.

The following examples are provided to illustrate the present invention and are not to be construed to be limiting thereof.

EXAMPLES

Example 1

Experimental procedure for use of the present invention's method to identify internalization targets.

Preparation of Target and Control Cells

1. Wash the target cells (transfected or antigen positive) and control cells (mock-transfected or antigen negative) 3× with 5% FCS[1]/PBS[2] or with PBS if cells will be fixed (see 2.2.3). TBS or HBS should be used if Ca2+ must be added to all buffers (see section 1.3; calcium precipitates in the presence of phosphate as calcium-phosphate).

[1] FCS: Fetal bovine serum: 0.1 μm sterile filtered, mycoplasma tested. PAN BiotechGmbH, Aidenbach, # 3302-P971610. (Or mycoplasma tested FCS from any other supplier.)
[2] PBS Dulbecco's: w/o calcium and magnesium and w/o sodium bicarbonate, Gibco BRL Life Technologies, #14190-094.

2. Count target cells and adjust to 5×106–1×107 cells in 1 ml 5% FCS/PBS in a 2 ml micro-centrifuge tube for each selection
3. Keep all subsequent steps at the appropriate temperature of 4° C. on ice for 2 h on an over head rotator at 4° C. for blocking.
4. Adjust phage titer of the combined library phage to 1-2×1013 phage in 1 ml 5% FCS/PBS (+suppl.). Incubate for 2 h at 4° C. for on an over-head rotator to block phage.

Selection on Target Cells

5. The blocked target cells are centrifuged at 2000 rpm for 2 min and resuspended in 0.5-1 ml pre-adsorbed phage-solution.
6. Incubate for 2 h at 4° C. on a rocker.

7. Spin cells at 2000 rpm for 2 min.
8. Carefully pipette off the supernatant and discard.
9. First Wash: carefully resuspend cell pellet in 1 ml 5% FCS/PBS (+suppl.) using a pipette.
10. Incubate for 5 min at 4° C.
11. Spin cells at 2000 rpm for 2 min.
12. Carefully pipette off the supernatant and discard.
13. Second Wash: carefully resuspend cell pellet in 1 ml 5% FCS/PBS (+suppl.) using a pipette.
14. Incubate for 5 min at 4° C. for live cells or at 20° C. for fixed cells on a rocker.
15. Spin cells at 2000 rpm for 2 min.
16. Carefully pipette off the supernatant and discard.
17. Third Wash: carefully resuspend cell pellet in 1 ml 5% FCS/PBS (+suppl.) using a pipette. Transfer cells to a new sterile 2 ml tube that has been blocked with 5% FCS/PBS[3].

[3] This step helps to avoid again enrichment of phage un-specifically bound to the selection tube.

18. Incubate for 5 min at 4° C. for live cells or at 20° C. for fixed cells on a rocker.
19. Spin cells at 2000 rpm for 2 min.
20. Carefully pipette off the supernatant and discard.

Internalization of Phage:
21. Carefully resuspend cell pellet in 1 ml 5% FCS/PBS (+suppl.) using a pipette.
22. Increase temperature to 37° C. and incubate for 30 min Depletion of not Internalized Phage
23. Add 300 μl 20 mM DTT in 10 mM Tris/HCl, pH8.0[4] to the cells and incubate for 10 min at RT[5], spin at 2000 rpm for 2 min, discard supernatant

[4] 20 mM DTT in 10 mM Tris/HCl, pH 8.0: the DTT solution should always be stored at −20° C. Avoid multiple freezing and thawing of the solution.
   [5] Instead of DTT elution, which is recommended for the HuCAL GOLD® library, conventional elution methods can also be used (e.g., see Krebs et al., 2001)

24. Fourth Wash: carefully resuspend cell pellet in 1 ml 5% FCS/PBS (+suppl.) using a pipette.
25. Incubate for 5 min at 4° C.
26. Spin cells at 2000 rpm for 2 min.
27. Carefully pipette off the supernatant and discard.
28. Fifth Wash: carefully resuspend cell pellet in 1 ml 5% FCS/PBS (+suppl.) using a pipette.
29. Incubate for 5 min at 4° C. for live cells or at 20° C. for fixed cells on a rocker.
30. Spin cells at 2000 rpm for 2 min.
31. Carefully pipette off the supernatant and discard.

Recovering of Internalized Phase
32. Add 500 μl 100 mM triethylamine (140 μl TEA in 10 ml PBS) and incubate for 10 min at RT (cells tend to lyse immediately). Add 400 μl 1M Tris pH 7.0 for neutralization. Check pH after neutralization with pH-indicator stick.
33. Use eluate for infection of TG1 (DWCP)
34. Identify and express Fab expressing clones by standard procedures.

Example 2

Antigen A, B and C were tested for prevalence on cell and Fab A, B, C for internalization properties.

Materials and Methods:
Fabs Tested:
 Fab_C_FH (Lysozyme binder, negative control)
 Fab_B_FS (ICAM binder, non internalizing control)
 Fab_A_FH (antigen A, internalizing)
 Fabs tested at 1 μg/ml
Cells:
 NCI H226: lung carcinoma cells
 1×10E5 cells/measurement Other Material:
 10% Saponin: 1 g Saponin was dissolved in 10 ml PBS, 0.5% Saponin/PBS, stored at 4 C
 4% PFA: stocksolution 16% was diluted 1:4 in PBS. Stock-solution: 16% w/v Alpha Aesar, Lot E10S015
 FACSbuffer (FB): PBS/3% FCS, stored at 4 C
 Goat anti human IgG (H+L)-PE, Jackson Dianova, 109-116-088, diluted 1:200 in FACS buffer (PBS/3% FCS)

Procedure:
1. 100 μl Fab (1 μg/ml) were added to a pellet of $2.5*10^6$ NCI H226 cells in FACSbuffer and incubated for one hour on ice. The cells were washed 2 times using 200 μl FACS-buffer, centrifuged (2000 rpm) and resuspended in 200 μl medium.
2. 100 μl were transferred to a 96 well plate and incubated for 1 h at 4° C. and further 10 min on ice.
3. The cells were washed 2 times 200 μl FACSbuffer; 200 rpm
4. Resuspended in 200 μl FACSbuffer, split in 2 times 100 μl and centrifuged 2 min 1200 rpm For Non Internalizing Conditions (4° C.):
For Extracellular Staining:
5. Cells were resuspended with 100 μl Goat anti human IgG-PE and incubated for 1 hour at 4° C. and washed two times with 200 μl FACSbuffer; 200 rpm
6. Resuspended in 100 μl FACSbuffer
7. FACS was then measured on BD FACSARRAY FSC 50; SSC; 280; Yellow 420

For Intracellular Staining:
8. Cells from step (4) were resuspended in 100 μl 4% PFA, 4° C. 30 min
9. Cells were washed 2 times with 200 μl FACSbuffer; 2000 rpm
10. Cells were resuspended in 0.5% Saporin, 10 min RT
11. 100 μl anti human IgG-PE were added and incubated for 1 h at RT
12. Cells were washed 2 times with 0.5% Saporin, 200 rpm
13. Resuspended in 100 μl FACSbuffer
14. FACS was then measured on BD FACSARRAY FSC 50; SSC; 280; Yellow 420

For Internalizing Conditions (37° C.):
For Extracellular Staining:
15. Cells from step (4) were resuspended with 100 μl Goat anti human IgG-PE and incubated for 1 hour at 37° C. and washed two times with 200 μl FACSbuffer; 200 rpm
16. Resuspended in 100 μl FACSbuffer
17. FACS was then measured on BD FACSARRAY FSC 50; SSC; 280; Yellow 420

For Intracellular Staining:
18. Cells from step (4) were resuspended in 100 μl 4% PFA, 4° C. 30 min
19. Cells were washed 2 times with 200 μl FACSbuffer; 2000 rpm
20. Cells were resuspended in 0.5% Saporin, 10 min RT
21. 100 μl anti human IgG-PE were added and incubated for 1 h at RT
22. Cells were washed 2 times with 0.5% Saporin, 200 rpm
23. Resuspended in 100 μl FACSbuffer
24. FACS was then measured on BD FACSARRAY FSC 50; SSC; 280; Yellow 420

Figure 1:
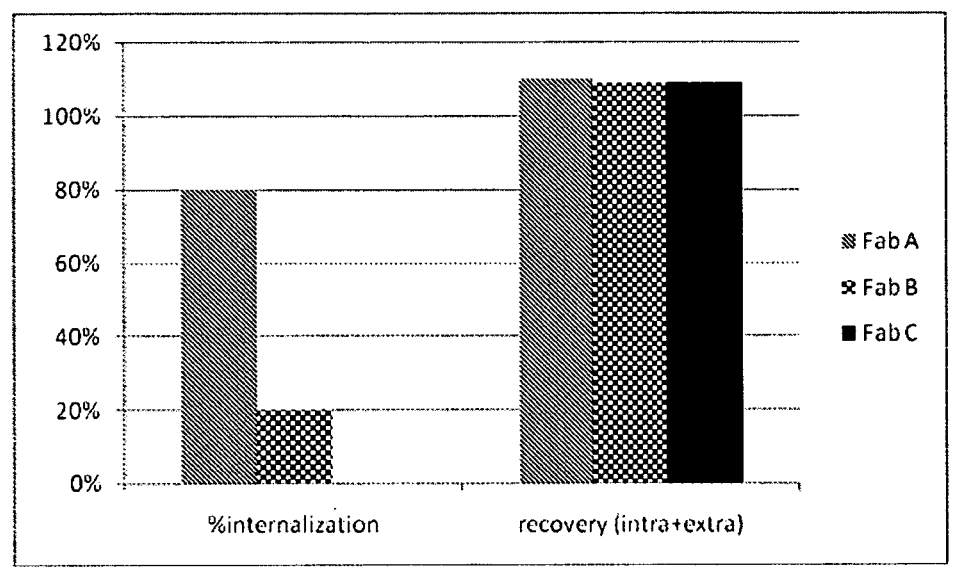
FIG. 1 shows efficiency of target internalization upon Fab binding.

Results:
As shown in FIG. 1, 80% of Fab target A were internalized as compared to only 20% of the Fab target B complex. The internalization process, cell permeabilization and staining did not influence the overall phage number.

Example 3

Enrichment of internalizing phages by DTT cleavage of extracellular bound phages Materials and Methods:
Phages Tested:
Genes encoding Fab A, B, C (see Example 1) were subcloned in Cys-Display vector pMORPH23 and VCSM 13 derived phages were produced according to standard procedures.
Phage_Fab_C (Lysozyme binder, negative control)
Phage_Fab_B_ (ICAM binder, non internalizing control)
Phage_Fab_A_ (antigen A, internalizing)
$1 \times 10E10$ phages each were used
Stripping:
20 mM DTT in 10 nM Tris/HCl pH 8.0, Roche Cat# 1583786
Antibodies:
Anti M13 mab: Amersham Biosciences, 27-9420-01, 1 mg/ml, to be diluted 1 µg/ml in FACS buffer FB (PBS/3% FCS)
Goat anti mouse IgG Fc gamma fragment specific-PE, Jackson Dianova, 115-116-071, R14, to be diluted 1:200 in FACS buffer (PBS/3% FCS)
Cells:
NCI H226: lung carcinoma cells
$1 \times 10E5$ cells/measurement
Other Material:
10% Saponin: 1 g Saponin was dissolved in 10 ml PBS, 0.5% Saponin/PBS
4% PFA: stocksolution 16% was diluted 1:4 in PBS. Stocksolution: 16% w/v Alpha Aesar, Lot E10S015
FACSbuffer (FB): PBS/3% FCS
Goat anti mouse IgG Fc gamma fragment specific-PE, Jackson Dianova, 115-116-071, R14, to be diluted 1:200 in FACS buffer (PBS/3% FCS)
Procedure:
1. $1 \times 10E10$ phages were added to a pellet of $5*10^4$ NCI H226 cells in FACSbuffer and incubated for one hour at 4° C. The cells were washed 2 times using 400 µl FACSbuffer, centrifuged (2000 rpm) and resuspended in 600 µl medium.
For Non Internalizing Conditions (4° C.):
2. $2 \times 100$ µl were transferred to a 96 well plate and incubated for 1 h at 4° C. and further 5 min on ice.
3. The cells were washed 2 times 200 µl FACSbuffer; 200 rpm
4. Resuspended in 200 µl FACSbuffer, and centrifuged 2 min 2000 rpm
5. One control aliquot was resuspended in 100 µl, the second one in 50 µl DDT
6. The cells were stored on ice for 5 min and washed 2 time using 200 µl FACSbuffer and 1200 rpm
7. The cells were resuspended in 50 µl anti-M13 antibody (5 µg/ml FACSbuffer)
8. The cells were incubated 45 min at 4° C.
9. The cells were washed two times 200 µl FACSbuffer
10. The cells were resuspended in 100 µl Goat anti mouse IgG Fc gamma fragment specific-PE (1:100)
11. The cells were washed 2 times with 200 µl FACSbuffer
12. FACS was measured on BD FACSARRAY FSC 10; SSC335; Yellow 330
For Internalizing Conditions (37° C.):
13. $2 \times 100$ µl were transferred to a 96 well plate and incubated for 1 h at 37° C. and further 5 min on ice.
14. The cells were washed 2 times 200 µl FACSbuffer; 200 rpm
15. Resuspended in 200 µl FACSbuffer, and centrifuged 2 min 2000 rpm
16. One control aliquot was resuspended in 100 µl, the second one in 50 µl DDT
17. The cells were stored on ice for 5 min and washed 2 time using 200 µl FACSbuffer and 1200 rpm
18. The cells were resuspended in 50 µl anti-M13 antibody (5 µg/ml FACSbuffer)
19. The cells were incubated 45 min at 4° C.
20. The cells were washed two times 200 µl FACSbuffer
21. The cells were resuspended in 100 µl Goat anti mouse IgG Fc gamma fragment specific-PE (1:100)
22. The cells were washed 2 times with 200 µl FACSbuffer
23. FACS was measured on BD FACSARRAY FSC 10; SSC335; Yellow 330
Results:
Under the conditions of the experiment (with/without DTT, 4° C. or 37° C.) the cells stayed intact. As expected, cell binding of Phages bearing Fab C couldn't be detected.
As shown in FIG. 2, approximatly 65% of phage A and 20% of phage B were internalized when increasing the temperature from 4° C. to 37° C.
Phages on the cell surface could be effciently stripped by 5 min treatment with 20 mM DTT at 4° C., without influencing cell integrity.
DTT addition upon internalization stripped surface bound phages while leaving internalized ones intact thus allowing an enrichment of phages binding to internalizing targets.

The invention claimed is:
1. A method for recovering a nucleic acid molecule encoding a binding member of a complex internalized in a target cell, comprising the following steps of:
(a) contacting a target cell with a diverse collection of bacteriophage particles, wherein each or substantially all of said bacteriophage particles display a binding member on its surface, wherein said binding member is displayed as a non-fusion (poly)peptide with a phage coat protein of said bacteriophage particle and wherein each or substantially all of said bacteriophage particles comprise a nucleic acid molecule encoding the displayed binding member, wherein said display as a non-fusion (poly)peptide is characterized by a disulfide bond between the phage coat protein and the binding member,
(b) allowing for binding of the binding member displayed on the bacteriophage particle to its target, thereby allowing for the formation of at least one complex, each of said complexes comprising a bacteriophage particle with its displayed binding member and its target,
(c) culturing the target cell under conditions that allow internalization of at least one of said complexes into the cell,
(d) eluting the bacteriophage particles displaying a binding member that are not internalized under conditions that substantially no cell lysis occurs, wherein the eluting is carried out under reducing conditions such that said disulfide bond is cleaved,
(e) lysing the target cell comprising the internalized complexes, and
(f) recovering from the lysed cell the nucleic acid molecule encoding a binding member from at least one of the internalized complexes.
2. The method of claim 1, further comprising the step of determining the sequence of the target of the internalized complex.
3. The method of claim 1, wherein said disulfide bond is generated between a first cysteine residue comprised in said phage coat protein and a second cysteine residue comprised in said binding member.
4. The method of claim 1, wherein said recovery from the lysed cell of said nucleic acid molecule encoding the binding member is achieved by PCR.

5. The method of claim 2, wherein said step of determining the sequence of the target in the internalized complex is achieved by mass spectrometry.

6. The method of claim 2, wherein said recovery from the lysed cell of said nucleic acid molecule encoding the binding member is achieved by PCR.

7. The method of claim 3, wherein said recovery from the lysed cell of said nucleic acid molecule encoding the binding member is achieved by PCR.

\* \* \* \* \*